United States Patent [19]

Ringeisen et al.

[11] Patent Number: 4,605,012
[45] Date of Patent: Aug. 12, 1986

[54] APPLICATOR FOR SUPPLYING RADIO-FREQUENCY ENERGY TO AND FROM AN OBJECT

[75] Inventors: Victor Ringeisen, Wissembourg; Maurice Chivé; Serge Toutain, both of Lille, all of France

[73] Assignee: Odam, Societé Anonyme, Wissembourg, France

[21] Appl. No.: 569,400

[22] Filed: Jan. 9, 1984

[30] Foreign Application Priority Data

Jan. 11, 1983 [DE] Fed. Rep. of Germany ....... 3300677

[51] Int. Cl.⁴ .............................................. A61N 5/02
[52] U.S. Cl. ................................... 128/804; 128/653; 128/736; 219/10.55 R; 343/700 MS; 343/795; 374/122
[58] Field of Search ............... 128/804, 399, 736, 653; 343/700 MS, 767, 795, 829; 219/10.55 R, 10.55 F, 10.81, 10.79; 374/121, 122

[56] References Cited

U.S. PATENT DOCUMENTS 4,240,445 12/1980 Iskander et al. .................... 128/804
4,500,887 2/1985 Nester ........................... 343/700 MS

FOREIGN PATENT DOCUMENTS 539580 4/1973 U.S.S.R. .............................. 128/804

OTHER PUBLICATIONS

Bahl et al, "New Microstrip Slot Radiator . . .", Electronic Letters, 11 Sep. 1980, vol. 16, No. 19, pp. 731-732.

Primary Examiner—Lee S. Cohen
Attorney, Agent, or Firm—Erwin S. Teltscher

[57] ABSTRACT

An applicator for supplying radio-frequency energy (rf energy) to or from a high-loss material, preferably live tissue, to which a delimiting face of the applicator is to be applied in flat relationship, a double line being provided for transporting the energy, is characterized in that at least one conductor (3) of the double line extends substantially in parallel to the delimiting face and at least in its proximity. An applicator of this type is easy to produce (FIG. 1).

9 Claims, 7 Drawing Figures

APPLICATOR FOR SUPPLYING RADIO-FREQUENCY ENERGY TO AND FROM AN OBJECT

BACKGROUND OF THE INVENTION

The present invention relates to an applicator for supplying radio-frequency energy to or from a high-loss material, preferably live tissue, to which a delimiting face of the applicator is to be applied in flat relationship, a double line being provided for transporting the energy.

It has been previously known, in particular in the treatment of hyperthermia of the human body, to apply radio-frequency energy to the body surface by means of waveguides which permits the live tissue to be warmed up in a surface area depending on the size of the applicator, and a certain depth below such surface. It has been further known that the temperature can be determined by receiving the electro-magnetic radiation in the radio-frequency range emitted by the interested areas of the body (Planck's Radiation Law), which method, contrary to the determination of the temperature by means of the infrared radiation emitted by the body, permits determining not only the temperature of the surface, but also that of deeper regions.

A known applicator of the type TMO 3000/10000 from assignee comprises a rectangular hollow waveguide the hollow cross-section of which is filled with a dielectric. The delimiting surface of the applicator which is to be applied to the surface of the patient's body extends at a right angle relative to the longitudinal axis of the hollow waveguide. The known applicator is expensive to produce.

SUMMARY OF THE INVENTION

Now, it is the object of the present invention to improve an applicator of the type prescribed before so that it is easy to produce. According to the invention, this object is achieved in that at least one conductor of the double line extends substantially in parallel to the delimiting face and at least in its neighborhood. Accordingly, the longitudinal axis of this conductor, which corresponds at least approximately to the direction of travel of the radio-frequency energy passing through this conductor, extends in parallel to the delimiting face, contrary to the situation in the applicator described before. It has been found that surprisingly such applicators which are very easy to produce by making use of the printed circuit technology, can be so designed that they are suited for the intended application.

In the case of the applicator of the invention, the surface area of the conductor being provided next to the delimiting face is smaller than the surface area of the delimiting face. This permits the other conductor of the double line arrangement to influence the area of the measured and/or treated object which is covered up by the applicator.

According to one embodiment of the invention, the two conductors of the double line may be arranged in the same plane. In another preferred embodiment of the application which is realized in the examples which will be described later, the two conductors of the double line are, however, arranged in different planes. According to one preferred embodiment of the invention, the two conductors may be arranged in two planes extending substantially in parallel to each other. In order to keep the two conductors of the double line at a defined distance relative to each other and in a defined position, the man of the art is free to use technical solutions that would seem convenient to him. In a preferred embodiment of the invention, a dielectric disposed between the conductors takes substantially the form of a flat layer. The advantage of this arrangement is to be seen in the fact that it prevents in a very simple manner the two conductors from being short-circuited and facilitates at the same time keeping the two conductors in a defined position relative to each other.

According to one embodiment of the invention, the dielectric may preferably take the form of a board consisting of an insulating material and exhibiting at least a certain mechanical strength to give it sufficient self-supporting properties. These characteristics are, for instance, to be found in fiber glass reinforced epoxy resin boards of the type used for printed circuits.

In one embodiment of the invention, the conductors are at least partially realized in the manner of printed circuits, by metallization of a layer of insulating material which may consist of the board of insulating material mentioned before. The thickness of the metal coating applied by metallization in the range of 30 μm, as usually employed for printed circuits, is sufficient, at least for a great number of applications. So, the basic material usually employed for the production of printed circuits may be used for the production of the double line arrangement, and starting from this basic material the double line arrangement can be produced, at least to a great extent, by means of an etching process.

In one embodiment of the invention the two conductors exhibit, at least approximately, a complementary configuration so that one conductor extending in one plane—this conductor will be described herein as the second conductor—is recessed in the area where the other conductor extending in the other plane—which conductor will be described herein as the first conductor—is located. According to one embodiment of the invention, the said recess in the second conductor and the shape of said first conductor may be almost congruent. However, it has been found to be advantageous, in particular in applicators for very high frequencies, to make the recess in the one conductor greater than the area of the other conductor and further to provide for certain differences in shape between the recess on the one hand and the shape of the other conductor on the other hand.

According to one embodiment of the invention, the said first conductor increases in a wedge-like manner, starting from a connection point by which it is to be connected to a radio-frequency supply line, preferably symmetrically to a plane passing through the connection line. The shape of the end in the area of the largest cross-section of this wedge-shaped portion may be selected as required. In one embodiment of the invention, the end is straight so that the said first conductor has substantially the shape of an isosceles triangle.

In another embodiment of the invention, the enlarged wedge-type portion is followed by a portion resembling substantially the area of a semi-circle. This embodiment has proven its value for applicators of larger surface intended, for instance, for being applied to the human thorax.

According to an improvement of an applicator which according to the before-described embodiment comprises a conductor exhibiting a recess which is at least approximately complementary to the shape of another conductor, the recess in the second conductor which corresponds in shape substantially to the first conductor is missing in the area of the pointed end of the wedge-type portion. One advantage offered by this arrangement is to be seen in the fact that there is no interruption in the second conductor in the area of the pointed end of the wedge-shaped section so that according to certain preferred embodiments of the invention the second conductor encloses the recess all around.

In one embodiment of the invention, the second conductor comprising the recess is arranged closer to the delimiting face than the first conductor, preferably even within the said delimiting face, and the second conductor is connected to ground in a manner suited for radio-frequencies. Then, the second conductor may for instance be conductively connected to the patient's body when the applicator is applied to the latter. This embodiment of the invention has proven its value in particular for applications where effective warming-up is to be achieved within a defined area and over a notable depth. Due to the fact that one conductor is connected to ground, the applicator can be simply fed via coaxial lines establishing the connection to a radio-frequency transmitter and/or receiver. The described applicators offer the advantage that when used for hyperthermia, i.e. when the applicator is fed with radio-frequency energy by a transmitter, almost no energy is emitted by the applicator when the latter is not applied to the body under treatment, which means that the applicator itself is no antenna, and that a considerable amount of energy can be transmitted to the human body as soon as the applicator is applied to the latter.

Further advantages of the invention are to be seen in the fact that when suitable designs, i.e. in particular the before-designed embodiments with a wedge-shaped conductor are selected, the applicator offers a wide frequency range so that it can be used selectively in the range of 434 MHz, in the range of 915 MHz and in the range of 2.45 GHz. However, its technical design enables the applicator also to work in any ranges between the said frequencies (IMS frequencies).

The frequencies of approx. 434 MHz and 915 MHz are preferably used for transmitting, i.e. for warming-up the body under treatment, whereas the frequency of approx. 2.45 GHz is the incoming frequency which is evaluated for determining a temperature of the volume under treatment. Depending on the level of any interfering frequency that may be produced, for instance, by television transmitters, other frequency ranges may be selected for the incoming frequency thanks to the broad frequency range provided by the applicator.

Of the embodiments of an applicator that will be described hereafter, the smallest one is intended for the frequency range of 10 GHz.

In one embodiment of the invention, one conductor takes substantially the form of a strip conductor which extends along one side of the layer of insulating material and which is connected to the central portion of the other conductor by means of a conductive section passing through a recess provided in the layer of insulating material, and the other conductor is provided with slots extending substantially radially to the said conductive section. The said slots act as slot radiators so that they also supply radio-frequency energy for warming-up a defined volume area when the applicator is applied to the human body.

In one embodiment of the invention, the slots have different resonance frequencies, which may be achieved by giving the slots different lengths. This gives the whole arrangement a greater electric band width. Preferably, three or more slots are provided.

In one embodiment of the invention, the applicator comprises an electrically conductive housing enclosing those parts of the applicator which are located behind the delimiting face. This offers the dual advantage that on the one hand the housing acts as mechanical protection and handle for the applicator, while preventing on the other hand radio-frequency from being emitted in a direction away from the body to be treated. Even if this energy may be very low, it is certainly desirable to protect the treating persons from being unnecessarily exposed to electromagnetic radiation. The housing is preferably connected to ground in a manner suitable for radio-frequencies.

In treating patients it is very often desirable to ensure that the surface of the skin area getting in direct contact with the applicator is not heated up beyond a pre-determined temperature limit as this may be disagreeable or even detrimental to the patient. In order to cool the skin in such cases, one embodiment of the invention provides that at least one of the conductors is thermally connected to the housing. This offers the advantage that any thermal energy taken up by the conductor is transmitted by a thermal connection to the housing from where it is dissipated by convection thanks to its relatively large surface.

In one embodiment of the invention a block consisting of a metal of high thermal conductivity and connected to the housing is superimposed upon the conductor facing away from the delimiting face, with a layer of an insulating material being interposed between the block and the conductor. This allows particularly efficient dissipation of the thermal energy. The block influences the equivalent circuit diagram of the applicator. To adapt the input of the applicator, to which a connection line leading to a transmitter or receiver is connected, to this connection line, a compensation is normally necessary. Surprisingly, it has been found that broadband compensation is particularly easy when the cross-section of the block taken in parallel to the plane of the conductor with which the block is thermally connected is smaller than the area of the said conductor and when the block does not project at any point beyond the said conductor. Such an arrangement has been found to be particularly advantageous when the dimensions of the said cross-section of the block, measured in any direction, do not exceed about half the corresponding dimensions of the said conductor, and when there is a substantially uniform distance between the edge of the conductor and the outside of the block. In this case, the presence of the block has no detrimental effects on the adaptation of the applicator.

BRIEF DESCRIPTION OF THE DRAWINGS

Other features and advantages of the invention will become apparent from the claims and the following description of certain examples of the invention when read with reference to the drawings, it being understood that the individual features of the invention may be realized in the different embodiments of the invention either individually or in any desired combination. In the drawings

DETAILED DESCRIPTION OF ILLUSTRATIVE EMBODIMENT

Figure 1:
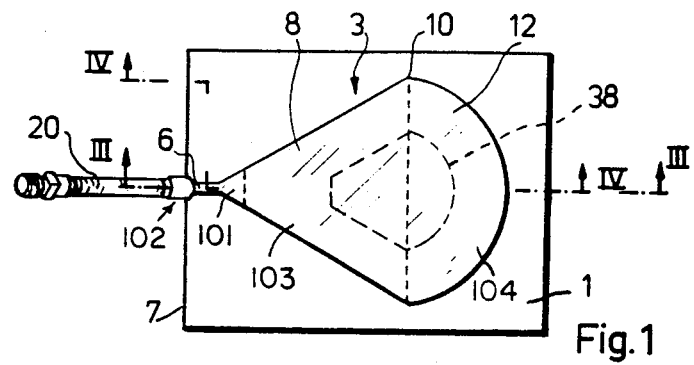
FIG. 1 is a top view of the printed circuit board of a first example of an applicator.

In FIGS. 1 to 4, a board 1 made of an insulating material can be seen which had been originally provided with a continuous metallic coating on both sides which was later partially removed by etching. The board 1 carries on the face which is visible in FIG. 1 a first conductor 3, and on the other face a second conductor 4. The first conductor comprises a strip-like section 6 extending from the center of the left edge 7—as viewed in FIG. 1—a short distance towards the center of the board 1. The said section 6 is followed by a portion 8 increasing in a wedge-like manner symmetrically to the sectional plane III—III. The wider end of this wedge-like portion is in turn followed by a section 12 in the form of a semi-circle so that the shape of the first conductor 3 narrows again on its right-hand end. The diameter of the semi-circle 12 is substantially equal to the dimension of the widest point 10. The second conductor 4 which is arranged on the bottom face of the applicator extends on all sides right to the edge of the insulating board 1 and formed with a recess a recess 14 defined by straight edges 15, 16 and 17 and one semi-circular edge 18. The edges 15, 16 and 18 are congruent to the corresponding edges of the first conductor 3, with the exception that the shape of the recess 14 deviates from the shape of the first conductor 3 in the area of the straight edge 17 opposite the semi-circular edge 18. In other words, the first conductor 3 increases from a pointed end region 101 near a connection zone 102 to a truncated wedge-like broader region 103, which, in turn, is followed by an end part 104 having substantially the shape of a semi-circle. The second conductor 4 is continuous in shape where the first conductor 3 exhibits its strip-like portion and starts to widen in a wedge-type manner.

The two conductors 3 and 4 are connected to a rigid coaxial line 20 which forms part of a connection line leading to the unit to which the applicator is to be connected. The inner conductor of the coaxial line 20 is soldered to the strip-like conductor 6, the outer conductor to the second conductor 4. The coaxial line 20 is fastened in the area of the left edge 7—as viewed in FIG. 1—which corresponds to a narrow edge of the rectangle formed by the printed circuit board 1, and extends upwardly at a suitable angle, which in the described example is approx. equal to 45°.

The characteristic impedance of the coaxial line 20 is 50 Ohms and the double line or transmission line formed by the strip-like conductor 6 and the opposite portion of the second conductor 4 has the same characteristic impedance, just as the remaining portions of the double line formed by the two conductors 3 and 4. During operation, the printed circuit board 1 is applied by its lower edge, i.e. the second conductor 4, to an area of a human body, and the applicator is supplied with radio frequency via the coaxial line 20. Reflections of the radio frequency energy are not encountered at all or only in a non-disturbing degree.

The fact that due to the wedge-like configuration the dimensions of the conductors do not change suddenly, but rather gradually, gives the applicator a considerable bandwidth.

Figure 2:
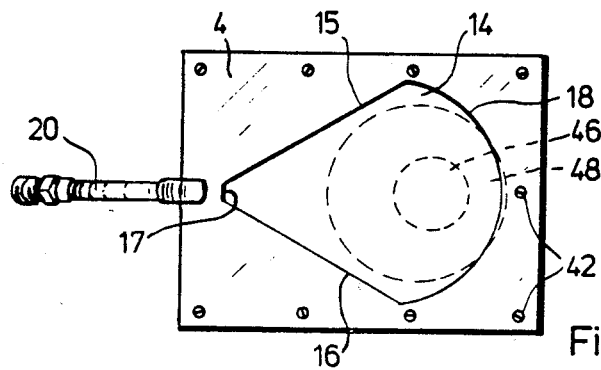
FIG. 2 is a bottom view of the printed circuit board of FIG. 1.
Figure 3:
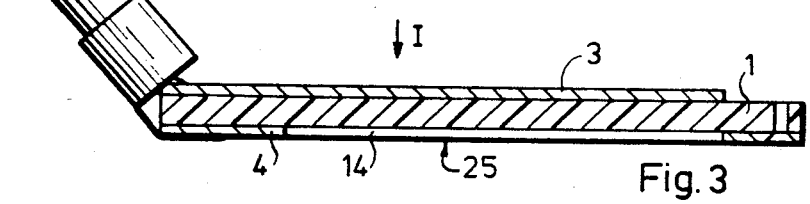
FIG. 3 shows a longitudinal section taken along line III—III in FIG. 1 through the printed circuit board and the connected connection line only, in a larger scale than that used in FIG. 1.

The applicator shown in FIGS. 1 to 3 which is composed substantially by the printed circuit board 1 carrying the conductors 3 and 4 only, may either be used in this form or may be enclosed by a having to facilitate the handling of the conductor, which housing extends upwardly from the delimiting face 25, i.e. the plane of the second conductor 4, to cover the first conductor 3. Such a housing provides also a protection against electric contact between the conductor 3 and the operator, and a mechanical protection for the printed circuit board 1.

The applicator shown in FIGS. 1 to 4 includes a metallic housing 30 having a box-like structure. The bottom side of the housing 30 is open, the surrounding walls 32 are provided on their lower ends with a shoulder 34 which serves as support for the printed circuit board 1. The second conductor 4 extends downwardly and outwardly. A film of insulating material 36 is placed upon the first conductor 3, and an aluminium block 38 which has its face opposite the film 36 in firm contact with the inner face of the upper wall 40 of the housing 30 is superimposed upon the film 36. The printed circuit board 1 is fixed to the housing 30 by means of screws 42 the position of which is also indicated in FIG. 2. The block 38 is in intimate contact with the film 36, and the latter is in intimate contact with the first conductor 3 so that a sufficiently good thermal connection is established between the first conductor 3 and the housing 30, giving due consideration to the properties and thickness of the material of the electrically insulating film 36. The cross-section of the block 38, taken in parallel to the delimiting face 25, is smaller than the area of the first conductor 3, and the block 38 does not extend at any point to, or even beyond, the edge of the first conductor 3. The cross-section of the block 38 is largely adapted to the shape of the conductor 3, and its dimensions are selected to ensure that they correspond substantially to about half the respective dimensions of the first conductor 3. The described cross-section of the block 38, and its position above the first conductor 3, are shown in broken lines in FIG. 1.

In a first realization of the example shown in FIGS. 1 to 4, which is primarily intended for a transmitter frequency of 434 MHz, the rectangular insulating board 1 which is made of fiber glass reinforced epoxy resin, has a size of 125 mm×106 mm and a thickness of 1.5 mm. The conductor section 6 is 2.8 mm in width. The widest point 10 of the first conductor 3 has a width of 77 mm. The remaining dimensions can be taken from FIGS. 1 and 2, giving due regard to the statements contained herein. The metal coatings forming the conductors 3 and 4 have a thickness in this example, just as in the other examples, of 30 $\mu$m. The film 36 consists of polyester on the basis of ethylene glycol and terephthalic acid (Mylar) and has a thickness of 30 $\mu$m. The block 38 is about 15 mm high.

Figure 4:
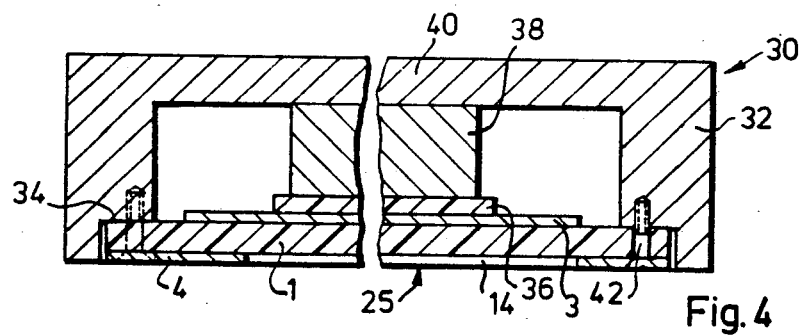
FIG. 4 shows a section taken along line IV—IV in FIG. 1 through a complete applicator with housing, but partially broken away.

FIGS. 3 and 4 are not true to scale, in particular as regards the thicknesses of the printed circuit board 1 and the conductors 3 and 4, and of the film 36.

An applicator having the dimensions just described is suited, due to the relatively large area of the recess 14, for treating larger surface areas of the human body. The radio frequency energy causes the human body to heat up, and this mainly in a volume area extending substantially below a surface area 46—measured vertically to the delimiting face 25—near the center of the recess 14 which area 46 is indicated in broken lines in FIG. 2. A little less heat, compared with the aforementioned area, is developed in an area 48 around the said surface area 46. This area 48 is likewise indicated by broken lines.

In another form of implementation or realization of the invention, which lends itself particularly well for treating smaller areas of the human body, for instance the hand, the printed circuit board 1 has a length of 90 mm and a width of 68 mm. The thickness of the printed circuit board 1 is again 1.5 mm. For the rest, the first conductor 3 and the recess 14 are only reduced in scale as compared with the realization of the invention described first so that FIGS. 1 to 4 apply also to this second realization which is intended for applying radio frequency energy at a frequency of about 915 MHz.

For determining the temperature of the area of the human body which is heated up by the application of radio frequency energy the radiant energy of the human body in the range of about 2500 MHz is received by the applicators in both realizations described above and transmitted to a connected electronic evaluation unit for evaluation.

Figure 5:
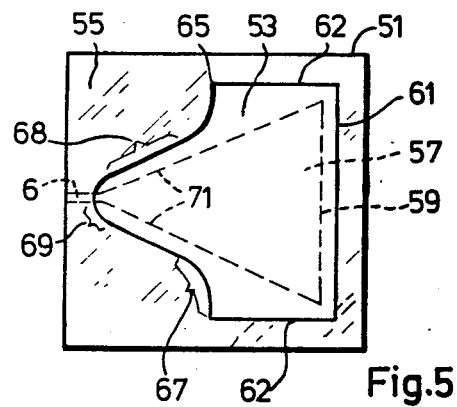
FIG. 5 shows a view similar to FIG. 2 of the printed circuit board of another example of an applicator.

The printed circuit board 51 of an applicator shown in FIG. 5 is formed with a recess 53 in the second conductor 55 which is notably larger than the area of the first conductor 57, with the edge of the recess 53 projecting on all sides beyond the edge of the first conductor 57. But here again, as in the case of the applicator in accordance with FIGS. 1 to 4, the second conductor 55 is not interrupted in the area of the strip-like section. Contrary to FIGS. 1 to 4, the first conductor 57 does not have any semi-circular area. Instead, the wedge-type portion of the first conductor 57 ends in a straight edge 59 at the side of the first conductor 57 opposite the connection to the radio frequency line. The recess 53 also has a straight edge 61 in the area of the edge 59, the two edges extending in parallel to each other. From the edge 61 there extend at a right angle edges 62 of the recess 53. The edges 62 extend in parallel to the longitudinal edge of the printed circuit board 51, and beginning at the end 65 of the edges 62 opposite the edge 61 the contour of the recess 53 extends symmetrically to the longitudinal center plane of the arrangement along slightly S-shaped curves so that the end 65 is first followed by a concave section 67, then by a straight section 68 and finally by a convex section 69 of the edge of the recess 53. The straight sections 68 include between them almost the same angle as the edges 71 of the first conductor 57 which extend away from each other in the form of a wedge.

In one form of realization of the invention, the printed circuit board 51 has the shape of a square with an edge length of 12 mm and a thickness of 0.8 mm. The exact dimensions of the recess 53 and of the first conductor 57 can be taken from FIG. 5, giving due consideration to the mentioned edge length of the printed circuit board 51. The material of the printed circuit board 51 is in this case polytetrafluorethylene which is suited for microwaves.

The form of realization just described may of course be used for applying radio frequency energy to the human body, but is mainly intended for measuring the temperature existing in the human body, by picking up the electromagnetic radiation in the range of 10 GHz.

Figure 6:
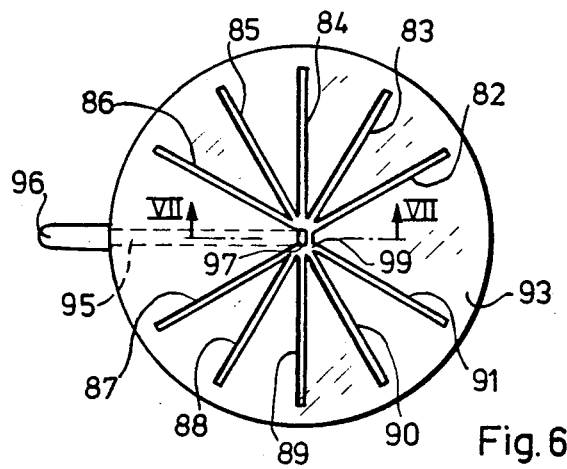
FIG. 6 shows a bottom view of the printed circuit board of an applicator with slots.

In the embodiment shown in FIG. 6, a board consisting of an insulating material 81 carries on its side visible in FIG. 6 a metal coating which is interrupted by radial slots 82 to 91 and which forms the second conductor 89. The radially inner ends of the slots 82 to 91 open into a common recess 99 of the second conductor 93. As can be clearly seen in FIG. 6, the width of this recess 99 is notably smaller at that point in the area of the metal band 98 which faces away from the first conductor 95 than in all other areas. The other face of the printed circuit board 81 is provided only with a strip-like conductor 95 connected to the middle conductor of a coaxial line 96, while the conductor 93 is connected to the outer conductor of the same coaxial line 96. The circular printed circuit board is provided at its center with an oblong hole 97 forming the passage for a metal band 98 which is soldered to both the first conductor 95 and the second conductor 93. The individual slots 82 to 91 are identical in length and width. They are not uniformly distributed over the whole circular face of the printed circuit board 81, but they extend substantially radially to the oblong hole 79, and in mirror-symmetrical arrangement to a plane of symmetry passing through the first conductor 95. The slots 84 and 89 which extend on either side of the said plane form a right angle therewith, while the individual slots of the two groups of slots 82 to 86 and 87 to 91 are equally spaced at an angle of about 30° C.

In the example shown the printed circuit board 81 has a diameter of 90 mm, and the ten slots 82 to 91 are each 1.5 mm wide and 40 mm long. The useful frequency range thereby obtained for the applicator of FIGS. 6 and 7 is about 400 MHz to 4000 MHz.

Figure 7:
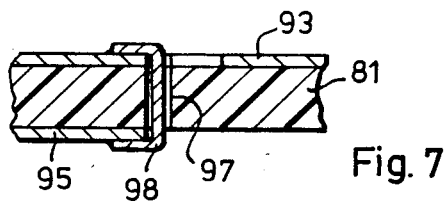
FIG. 7 shows an enlarged sectional view taken along line VII—VII in FIG. 6.

In the applicator shown in FIGS. 6 and 7, the delimiting surface to be applied to the human body is again formed by the face of the second conductor 93 which is connected to ground in a manner suited for radio frequencies. And again, this embodiment may also be provided with a housing if this should be desired.

The applicators of the invention have all electrodes or conductors arranged on the same side of the tissue which means that the tissue does never get between the conductors.

The reference numerals in the patent claims do not constitute a limitation, but are merely to facilitate understanding of the claims.

We claim:

1. An applicator for coupling electromagnetic energy into a high-loss material, such as tissue, comprising in combination a transmission line having first and second conductors (3,4) disposed in different respective planes, a substrate (1) of insulating material interposed between said conductors (3,4), said substrate (1) being in firm mechanical relationship with said conductors (3,4), said conductors (3,4,) having an at least approximately complementary configuration, so that said first conductor (3), which is disposed in one plane, increases in width from a substantially pointed end region (101) near a connection zone (102) adapted to be connected to a radio frequency supply line carrying frequencies at least within the range of about 434 MHZ to about 2.45 GHz, to a truncated wedge-like broader region (103) widening as its extends away from said connection zone (102), said truncated wedge-like broader region (103) merging smoothly with said pointed end region (101), while said second conductor (4), which is disposed substantially in the other plane, defines on a portion thereof a delimiting face (25) facing outwardly, which is adapted to be in substantially flat relationship with said high-loss material, said second conductor being further formed with a recess (14) extending substantially only opposite said broader region (103) of said first conductor (3), and having opposite said broader region (103) substantially the shape of said first conductor (3), at least one of the remaining portion of said second conductor (4) and said first conductor (3) extending substantially in parallel with said delimiting face (25) and in proximity thereto, whereby said transmission line may radiate electromagnetic energy within a bandwidth of at least 2 GHz.

2. The applicator according to claim 1, wherein said delimiting face (25) has a predetermined surface area, and said second conductor (4) has a surface area situated next to said delimiting face (25) which is smaller than said predetermined surface area.

3. The applicator according to claim 1, wherein said planes extend substantially parallel to one another.

4. The applicator according to claim 1, wherein said substrate (1) of insulating material includes a substantially flat dielectric layer.

5. The applicator according to claim 1, wherein said conductors (3,4) take the form of metallic coatings on said substrate (1).

6. The applicator according to claim 1, wherein an end part (104) of said first conductor (3) adjoining said broader region (103) and opposite said pointed end region (101) has substantially the shape of a semi-circle.

7. The application according to claim 1, wherein said recess (14) formed in said second conductor (4) is defined by a continuous inner peripheral border.

8. An applicator for coupling electromagnetic energy into a high-loss material, such as tissue, comprising in combination a transmission line having first and second conductors (3,4,) disposed in different respective planes, a substrate (1) of insulating material interposed between said conductors (3,4), said substrate (1) being in firm mechanical relationship with said conductors (3,4), said second conductor (4) defining on a portion thereof a delimiting face (25) facing outwardly, which is adapted to be in substantially flat relationship with said high-loss material, at least one of the remaining portion of said second conductor (4) and said first conductor (3) extending substantially in parallel with said delimiting face (25), and in proximity thereto, an electrically conductive housing (30) surrounding said first conductor (3), said substrate (1) and said second conductor (4) on at least three respective sides thereof, a block (38) made of a metal with high thermal conductivity, and abutting said housing (30), and an insulating layer (36) in contact with one side thereof with said block (38), and in contact with another side thereof opposite said one side with said first conductor (3), whereby said first conductor (3) is thermally connected to said housing (30).

9. An applicator for coupling electromagnetic energy into a high-loss material, such as tissue, comprising in combination a transmission line having first and second conductors (3,4,) disposed in different respective planes, a substrate (1) of insulating material interposed between said conductors (3,4), said substrate (1) being in firm mechanical relationship with said conductors (3,4), said first conductor (3), which is disposed in one plane, increasing in width from a substantially pointed end region (101) near a connection zone (102) adapted to be connected to a radio frequency supply line carrying frequencies at least within the range of about 434 MHZ to about 2.45 GHz, to another broader region (103) widening as it extends away from said connection zone (102), said other broader region (103) merging smoothly with said pointed end region (101), said second conductor (4), which is disposed substantially in the other plane, defining on a portion thereof a delimiting face (25) facing outwardly, which is adapted to be in substantially flat relationship with said high-loss material, said second conductor being further formed with a recess (14) extending substantially at least opposite said broader region of said first conductor (3), at least one of the remaining portion of said second conductor (4) and said first conductor (3) extending substantially in parallel with said delimiting face (25) and in proximity thereto.

* * * * *